United States Patent [19]

Senn-Bilfinger

[11] 4,363,816
[45] Dec. 14, 1982

[54] TRICYCLIC PYRROLES, THEIR COMPOSITIONS AND THEIR USE

[75] Inventor: Jörg Senn-Bilfinger, Constance, Fed. Rep. of Germany

[73] Assignee: BYK Gulden Lomberg Chemische Fabrik Gesellschaft mit beschrankter Haftung, Constance, Fed. Rep. of Germany

[21] Appl. No.: 344,172

[22] Filed: Jan. 29, 1982

[30] Foreign Application Priority Data

Feb. 2, 1981 [CH] Switzerland .......................... 651/81
Aug. 26, 1981 [CH] Switzerland .......................... 5488/81

[51] Int. Cl.³ ..................... A61K 31/55; C07D 487/04
[52] U.S. Cl. ............................. 424/274; 260/239.3 T; 424/263; 424/248.54; 424/250
[58] Field of Search ................. 260/239.3 T; 422/274; 424/248.54, 250, 263

[56] References Cited

U.S. PATENT DOCUMENTS 4,185,016  1/1980  Takanabe et al. ............ 260/239.3 T Primary Examiner—Robert T. Bond
Attorney, Agent, or Firm—Berman, Aisenberg & Platt

[57] ABSTRACT

1,4,9,10-tetrahydropyrrolo[3,2-b][1,5]benzodiazepin-10-ones have been found to provide excellent protection for the stomach and intestines of warm-blooded animals. They are useful for the treatment and prophylaxis of such maladies as gastritis, acute and chronic ulcus ventriculi and hyperacid gastric irritation. The compounds are administered enterally or parenterally, usually in a standard dosage form. The disclosure includes key intermediates, methods of synthesis, compositions and use.

17 Claims, No Drawings

TRICYCLIC PYRROLES, THEIR COMPOSITIONS AND THEIR USE

TECHNICAL FIELD

The invention relates to compounds, their use and medicaments containing them. The compounds are tricyclic pyrroles which are in free-base or acid-addition-salt form. They are used in the pharmaceutical industry as intermediates and for preparing medicaments. Pharmacologically-active and physiologically-acceptable embodiments are useful for prophylaxis or treatment of illness based on a stomach or intestine disorder.

STATE OF THE ART

Pyridobenzodiazepin-6-one derivatives with an ulcer-inhibiting, secreto-inhibiting, anti-tussive and, in some cases, anti-emetic action are claimed in German Auslegeschrift DE-AS 1,795,183 (U.S. Pat. No. 3,743,734), while pyridobenzodiazepin-5-ones with a purely anti-tussive action are reported in DE-AS 1,620,523 (U.S. Pat. No. 3,455,727). Cyclopentabenzodiazepinones with an analgesic and anxiety-reducing activity are considered in Japanese Preliminary Published Application 54-135,788. Further tricyclic compounds with tranquilizing and antihypertensive activity are referred to in German Offenlegungsschrift DE-OS No. 2,050,344 (U.S. Pat. No. 3,598,809).

THE INVENTION

A class of new tricyclic pyrroles, which are neither mentioned in nor suggested by these publications, has now been synthesized. These tricyclic pyrroles have interesting and particularly advantageous pharmacological properties. The invention actually relates to all tricyclic pyrroles of formula I

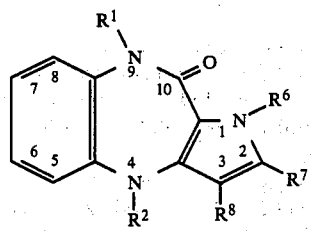

wherein
$R^1$ denotes a hydrogen atom (—H) or a lower alkyl radical, particularly one with from 1 to 4 carbon atoms,
$R^2$ denotes the group —CO—$C_nH_{2n}$—$R^3$ or a hydrogen atom (—H),
$R^3$ denotes a halogen atom or the group —N($R^4$)$R^5$,
$R^4$ denotes a hydrogen atom (—H), a lower alkyl radical, particularly one with from 1 to 4 carbon atoms, or an alkenyl radical with from 3 to 5 carbon atoms and
$R^5$ denotes a lower alkyl radical, particularly one which has from 1 to 4 carbon atoms, which is optionally substituted by a di(lower)alkylamino group, e.g. one with from 1 to 4 carbon atoms in each alkyl radical, or denotes an alkenyl radical with from 3 to 5 carbon atoms, or
$R^4$ and $R^5$ together, with the inclusion of the nitrogen atom to which both are bonded, denote a pyrrolidino, piperidino, morpholino or perhydroazepino ring, a 1-piperazinyl radical which is optionally substituted in the 4-position by a methyl, ethyl or benzyl group, or a 1-homopiperazinyl radical which is optionally substituted in the 4-position by a methyl group,
each of $R^6$, $R^7$ and $R^8$ is, independently, hydrogen (—H) or lower alkyl, e.g., with from 1 to 4 carbon atoms and
n represents 1 or 2,
and to their acid-addition salts with inorganic or organic acids.

Lower alkyl radicals are preferably those with from 1 to 4 carbon atoms, but 4 is not a critical upper limit. They are represented by methyl, ethyl, propyl, butyl, isopropyl, isobutyl, sec.-butyl and tert.-butyl radicals.

Alkenyl radicals with from 3 to 5 carbon atoms include, e.g., allyl and 2-methallyl radicals.

Illustrative halogen atoms are chlorine, bromine and iodine atoms, preferably the chlorine or bromine atom and especially the chlorine atom.

Contemplated salts include any possible acid-addition salts. The pharmacologically-acceptable salts of the inorganic and organic acids usually employed galenically are particularly important. Pharmacologically-unacceptable salts, which are optionally obtained initially, for example, as process products in the manufacture of the compounds according to the invention on an industrial scale, are readily converted into pharmacologically-acceptable salts by conventional processes known to the expert. Suitable pharmacologically-acceptable salts are, for example, water-soluble and water-insoluble acid-additon salts, such as the hydrochloride, hydrobromide, hydriodide, phosphate, nitrate, sulfate, acetate, citrate, gluconate, benzoate, hibenzate [2-(4-hydroxybenzoyl)benzoate], fendizoate, {o-[(2'-hydroxy-4-biphenylyl)carbonyl]benzoate}, butyrate, sulfosalicylate, maleate, laurate, malate, fumarate, succinate, oxalate, tartrate, amsonate (4,4'-diaminostilbene-2,2'-disulfonate), embonate (4,4'-methylene-bis-3-hydroxy-2-naphthoate), metembonate (4,4'-methylene-bis-3-methoxy-2-naphthoate), stearate, tosylate (p-toluenesulfonate), 2-hydroxy-3-naphthoate, 3-hydroxy-2-naphthoate and mesylate (methanesulfonate).

All compounds of formula I contain the identical tricyclic ring structure which is oxo-substituted in the 10-position. Those compounds of formula I which are physiologically active and pharmacologically acceptable are of particular interest.

Reference in this regard is especially made to tricyclic pyrroles of formula I:
wherein
$R^1$ represents a hydrogen atom (—H) or a lower alkyl radical,
$R^2$ represents the group —CO—$C_nH_{2n}$—$R^3$,
$R^3$ represents the group —N($R^4$)$R^5$,
$R^4$ represents a hydrogen atom (—H), a lower alkyl radical or an alkenyl radical with from 3 to 5 carbon atoms,
$R^5$ represents a lower alkyl radical and is optionally substituted by a di(lower)alkylamino group or represents an alkenyl radical with from 3 to 5 carbon atoms, or
$R^4$ and $R^5$ together, with the inclusion of the nitrogen atom to which both are bonded, denote a pyrrolidino, piperidino, morpholino or perhydroazepino ring, a 1-piperazinyl radical which is optionally substituted in the 4-position by a methyl, ethyl or benzyl group, or a 1-homopiperazinyl radical which is optionally substituted in the 4-position by a methyl group, $R^6$, $R^7$ and $R^8$ are identical or different and denote hydrogen (—H) or lower alkyl and n represents 1 or 2, and to their acid-addition salts with inorganic or organic acids, particularly the pharmacologically-acceptable salts. All of these compounds form one embodiment (a) of this invention.

Representatives of embodiment (a) which are of special importance include those in which $R^1$, $R^6$, $R^7$ and $R^8$ are identical or different and denote hydrogen (—H), methyl or ethyl; $R^2$ and $R^3$ have their previously-mentioned meanings; $R^4$ represents a hydrogen atom (—H), an alkyl radical with from 1 to 4 carbon atoms or an alkenyl radical with 3 carbon atoms; and $R^5$ represents an alkyl radical which has from 1 to 4 carbon atoms and is optionally terminally substituted by a dimethylamino or diethylamino group, or represents an alkenyl radical with 3 carbon atoms; or $R^4$ and $R^5$ (together with the nitrogen to which both are bound) represent a pyrrolidino, piperidino, morpholino, piperazino or 4-methyl- or 4-ethyl-1-piperazinyl group; and n denotes 1 or 2; and their acid-addition salts.

Preferred examples of embodiment (a) are those in which $R^1$ denotes a hydrogen atom (—H), $R^2$ and $R^3$ have their previously-ascribed meanings; $R^4$ denotes a hydrogen atom (—H) or an alkyl radical with from 1 to 4 carbon atoms; $R^5$ denotes an alkyl radical with from 1 to 4 carbon atoms and which is optionally terminally substituted by a dimethylamino group; or $R^4$ and $R^5$ (together with the nitrogen to which both are bound) denote a pyrrolidino, piperidino or morpholino ring or a 1-piperazinyl radical which is optionally substituted in the 4-position by a methyl group; $R^6$ denotes a methyl group; $R^7$ denotes a hydrogen atom (—H); $R^8$ denotes a methyl group; and n represents 1 or 2; and their pharmacologically-compatible acid-addition salts with inorganic or organic acids.

Particularly preferred representatives of embodiment (a) are those in which $R^1$ denotes a hydrogen atom (—H), $R^2$ and $R^3$ have their previously-ascribed meanings; $R^4$ denotes a hydrogen atom or a methyl, ethyl or propyl group; $R^5$ denotes a methyl, ethyl or propyl group; or $R^4$ and $R^5$ (together with the nitrogen to which both are bound) denote a pyrrolidino or piperidino ring or a 4-methyl-1-piperazinyl radical; $R^6$ denotes a methyl group; $R^7$ denotes a hydrogen atom (—H); $R^8$ denotes a methyl group; and n represents 1; and their pharmacologically-compatible acid-addition salts with inorganic or organic acids.

A second embodiment (b) of the invention comprises tricyclic pyrroles of formula I:

wherein $R^1$ represents a hydrogen atom (—H) or a lower alkyl radical, $R^2$ represents the group —CO—$C_nH_{2n}$—$R^3$, $R^3$ represents a halogen atom, $R^6$, $R^7$ and $R^8$ are identical or different and denote hydrogen (—H) or alkyl with from 1 to 4 carbon atoms, and n represents 1 or 2, and their acid-addition salts with inorganic or organic acids.

Noteworthy representatives of embodiment (b) are those in which $R^1$, $R^6$, $R^7$ and $R^8$ are identical or different and denote hydrogen (—H), methyl or ethyl; $R^2$ has its previously-noted meaning; $R^3$ represents chlorine (—Cl) or bromine (—Br); and n denotes 1 or 2; and their acid-addition salts.

Preferred examples of embodiment (b) are those in which $R^1$ denotes a hydrogen atom (—H), $R^2$ has its previously-designated meaning, $R^3$ represents chlorine (—Cl) or bromine (—Br), $R^6$ denotes a methyl group, $R^7$ denotes a hydrogen atom (—H), $R^8$ denotes a methyl group and n represents 1 or 2; and their acid-addition salts.

A third embodiment (c) of the invention comprises tricyclic pyrroles of formula I wherein $R^1$ represents a hydrogen atom (—H) or a lower alkyl radical, $R^2$ represents a hydrogen atom (—H) and $R^6$, $R^7$ and $R^8$ are identical or different and denote hydrogen (—H) or lower alkyl, and their acid-addition salts with inorganic or organic acids.

Illustrative representatives of embodiment (c) are those in which $R^1$, $R^6$, $R^7$ and $R^8$ are identical or different and denote hydrogen (—H), methyl or ethyl, and $R^2$ has its formerly-ascribed meaning; and their acid-addition salts.

Preferred representatives of embodiment (c) are those in which $R^1$ denotes a hydrogen atom (—H), $R^2$ has its previously-noted meaning, $R^6$ denotes a methyl group, $R^7$ denotes a hydrogen atom (—H), and $R^8$ denotes a methyl group; and their acid-addition salts.

Representative examples of compounds according to the invention are:

1,2,3,9-tetramethyl-4-[(4-methyl-1-piperazinyl)acetyl]-1,4,9,10-tetrahydropyrrolo[3,2-b][1,5]benzodiazepin-10-one, 1,2,3-triethyl-4-[(4-methyl-1-piperazinyl)acetyl]-1,4,9,10-tetrahydropyrrolo[3,2-b][1,5-benzodiazepin-10-one, 1,3-dimethyl-4-piperidinoacetyl-1,4,9,10-tetrahydropyrrolo-[3,2-b][1,5]benzodiazepin-10-one, 1,3-dimethyl-4-[(4-methyl-1-piperazinyl)acetyl]-1,4,9,10-tetrahydropyrrolo[3,2-b][1,5]benzodiazepin-10-one, 1,3-dimethyl-4-pyrrolidionacetyl-1,4,9,10-tetrahydropyrrolo-[3,2-b][1,5]benzodiazepin-10-one, 1-ethyl-2,3-dimethyl-4-piperidinoacetyl-1,4,9,10-tetrahydropyrrolo[3,2-b][1,5]benzodiazepin-10-one, 1,3-diethyl-9-methyl-4-[3-(4-methyl-1-piperazinyl)propionyl]-1,4,9,10-tetrahydropyrrolo[3,2-b][1,5]benzodiazepin-10-one, 1-methyl-4-[3-(piperidino)propionyl]-1,4,9,10-tetrahydropyrrolo[3,2-b][1,5]benzodiazepin-10-one, 1,9-dibutyl-4-[(4-methyl-1-piperazinyl)acetyl]-1,4,9,10-tetrahydropyrrolo[3,2-b][1,5]benzodiazepin-10-one, 1,2,3-triethyl-4-morpholinoacetyl-1,4,9,10-tetrahydropyrrolo-[3,2-b][1,5]-benzodiazepin-10-one, 1-isopropyl-2,9-dimethyl-4-piperidinoacetyl-1,4,9,10-tetrahydropyrrolo[3,2-b][1,5]benzodiazepin-10-one, 1-(n-butyl)-2,3,9-trimethyl-4-perhydroazepinoacetyl-1,4,9,10-tetrahydropyrrolo[3,2-b][1,5]benzodiazepin-10-one, 1,9-di-(n-butyl)-4-[(4-methyl-1-piperazinyl)acetyl]-1,4,9,10-tetrahydropyrrolo[3,2-b][1,5]benzodiazepin-10-one, 2-methyl-9-propyl-4-[2-(dimethylamino)propionyl]-1,4,9,10-tetrahydropyrrolo[3,2-b][1,5]benzodiazepin-10-one, 1,2,3-trimethyl-4-[N-(2-dimethylaminoethyl)-N-methylamino]-acetyl-1,4,9,10-tetrahydropyrrolo[3,2-b][1,5]benzodiazepin-10-one, 1,2,3-trimethyl-4-[3-(dibutylamino)propionyl]-1,4,9,10-tetrahydropyrrolo[3,2-b][1,5]benzodiazepin-10-one, 1,3,9-triethyl-4-piperidinoacetyl-1,4,9,10-tetrahydropyrrolo-[3,2-b][1,5]benzodiazepin-10-one, 1,3-di-(n-butyl)-9-ethyl-2-methyl-4-[(4-methyl-1-piperazinyl)-acetyl]-1,4,9,10-tetrahydropyrrolo[3,2-b][1,5]benzodiazepin-10-one, 9-(tert.-butyl)-1,2-dimethyl-4-perhydroazepinoacetyl-1,4,9,10-tetrahydropyrrolo[3,2-b][1,5]benzodiazepin-10-one, 1,3-dimethyl-4-[2-(dimethylamino)propionyl]-1,4,9,10-tetrahydropyrrolo[3,2-b][1,5]benzodiazepin-10-one, 1,3-dimethyl-4-[N-(2-dimethylaminoethyl)-N-methylamino]acetyl-1,4,9,10-tetrahydropyrrolo[3,2-b][1,5]benzodiazepin-10-one, 9-(n-butyl)-1,3-dimethyl-4-[(4-methyl-1-piperazinyl)acetyl]-1,4,9,10-tetrahydropyrrolo[3,2-b][1,5]benzodiazepin-10-one, 1,2,3-trimethyl-4-[3-(4-methyl-1-piperazinyl)propionyl]-1,4,9,10-tetrahydropyrrolo[3,2-b][1,5]benzodiazepin-10-one, 1,2-dimethyl-4-piperidinoacetyl-1,4,9,10-tetrahydropyrrolo[3,2-b][1,5]benzodiazepin-10-one, 1-methyl-2-propyl-4-[(4-methyl-1-piperazinyl)acetyl]-1,4,9,10-tetrahydropyrrolo[3,2-b][1,5]benzodiazepin-10-one, 9-isopropyl-1,3-dimethyl-4-piperidinoacetyl-1,4,9,10-tetrahydropyrrolo[3,2-b][1,5]benzodiazepin-10-one, 1,2,3-trimethyl-4-piperidinoacetyl-1,4,9,10-tetrahydropyrrolo[3,2-b][1,5]benzodiazepin-10-one, 1,2,3-trimethyl-4-[2-(4-methyl-1-piperazinyl)propionyl]-1,4,9,10-tetrahydropyrrolo[3,2-b][1,5]benzodiazepin-10-one, 9-methyl-4-[(4-methyl-1-piperazinyl)acetyl]-1,4,9,10-tetrahydropyrrolo[3,2-b][1,5]benzodiazepin-10-one, 9-methyl-4-piperidinoacetyl-1,4,9,10-tetrahydropyrrolo[3,2-b][1,5]benzodiazepin-10-one, 1,3-diethyl-4-[(4-methyl-1-piperazinyl)acetyl]-1,4,9,10-tetrahydropyrrolo[3,2-b][1,5]benzodiazepin-10-one, 1,3-diethyl-4-piperidinoacetyl-1,4,9,10-tetrahydropyrrolo[3,2-b][1,5]benzodiazepin-10-one, 1,2,3,9-tetramethyl-4-piperidinoacetyl-1,4,9,10-tetrahydropyrrolo[3,2-b][1,5]benzodiazepin-10-one, 1,2,3,9-tetramethyl-4-chloroacetyl-1,4,9,10-tetrahydropyrrolo[3,2-b][1,5]benzodiazepin-10-one, 1,2,3-triethyl-4-chloroacetyl-1,4,9,10-tetrahydropyrrolo[3,2-b][1,5]benzodiazepin-10-one, 1,3-dimethyl-4-chloroacetyl-1,4,9,10-tetrahydropyrrolo[3,2-b][1,5]benzodiazepin-10-one, 1,3-dimethyl-4-bromoacetyl-1,4,9,10-tetrahydropyrrolo[3,2-b][1,5]benzodiazepin-10-one, 1-ethyl-2,3-dimethyl-4-chloroacetyl-1,4,9,10-tetrahydropyrrolo[3,2-b][1,5]benzodiazepin-10-one, 1,3-diethyl-4-chloroacetyl-1,4,9,10-tetrahydropyrrolo[3,2-b][1,5]benzodiazepin-10-one, 1-methyl-4-bromoacetyl-1,4,9,10-tetrahydropyrrolo[3,2-b][1,5]benzodiazepin-10-one, 1,9-dibutyl-4-chloroacetyl-1,4,9,10-tetrahydropyrrolo[3,2-b][1,5]benzodiazepin-10-one, 1-isopropyl-2,9-dimethyl-4-chloroacetyl-1,4,9,10-tetrahydropyrrolo[3,2-b][1,5]benzodiazepin-10-one, 1-(n-butyl)-2,3,9-trimethyl-4-chloroacetyl-1,4,9,10-tetrahydropyrrolo[3,2-b][1,5]benzodiazepin-10-one, 1,9-di-(n-butyl)-4-chloroacetyl-1,4,9,10-tetrahydropyrrolo[3,2-b][1,5]benzodiazepin-10-one, 2-methyl-9-propyl-4-chloroacetyl-1,4,9,10-tetrahydropyrrolo[3,2-b][1,5]benzodiazepin-10-one, 1,2,3-trimethyl-4-chloroacetyl-1,4,9,10-tetrahydropyrrolo[3,2-b][1,5]benzodiazepin-10-one, 1,3,9-triethyl-4-bromoacetyl-1,4,9,10-tetrahydropyrrolo[3,2-b][1,5]benzodiazepin-10-one, 1,3-di-(n-butyl)-9-ethyl-2-methyl-4-chloroacetyl-1,4,9,10-tetrahydropyrrolo[3,2-b][1,5]benzodiazepin-10-one, 9-(tert.-butyl)-1,2-dimethyl-4-chloroacetyl-1,4,9,10-tetrahydropyrrolo[3,2-b][1,5]benzodiazepin-10-one, 9-(n-butyl)-1,3-dimethyl-4-bromoacetyl-1,4,9,10-tetrahydropyrrolo[3,2-b][1,5]benzodiazepin-10-one, 1-methyl-2-propyl-4-chloroacetyl-1,4,9,10-tetrahydropyrrolo[3,2-b][1,5]benzodiazepin-10-one, 9-isopropyl-1,3-dimethyl-4-chloroacetyl-1,4,9,10-tetrahydropyrrolo[3,2-b][1,5]benzodiazepin-10-one, 9-methyl-4-chloroacetyl-1,4,9,10-tetrahydropyrrolo[3,2-b][1,5]benzodiazepin-10-one, 1,3-diethyl-9-methyl-4-(3-chloropropionyl)-1,4,9,10-tetrahydropyrrolo[3,2-b][1,5]benzodiazepin-10-one, 1-methyl-4-(3-chloropropionyl)-1,4,9,10-tetrahydropyrrolo[3,2-b][1,5]benzodiazepin-10-one, 2-methyl-9-propyl-4-(2-chloropropionyl)-1,4,9,10-tetrahydropyrrolo[3,2-b][1,5]benzodiazepin-10-one, 1,2,3-trimethyl-4-(3-chloropropionyl)-1,4,9,10-tetrahydropyrrolo[3,2-b][1,5]benzodiazepin-10-one, 1,3-dimethyl-4-(2-chloropropionyl)-1,4,9,10-tetrahydropyrrolo[3,2-b][1,5]benzodiazepin-10-one, 1,2,3-trimethyl-4-(2-chloropropionyl)-1,4,9,10-tetrahydropyrrolo[3,2-b][1,5]benzodiazepin-10-one, 1,3-dimethyl-1,4,9,10-tetrahydropyrrolo[3,2-b][1,5]benzodiazepin-10-one, 1-ethyl-2,3-dimethyl-1,4,9,10-tetrahydropyrrolo[3,2-b][1,5]benzodiazepin-10-one, 1,3-diethyl-1,4,9,10-tetrahydropyrrolo[3,2-b][1,5]benzodiazepin-10-one, 1-methyl-1,4,9,10-tetrahydropyrrolo[3,2-b][1,5]benzodiazepin-10-one, 1,9-dibutyl-1,4,9,10-tetrahydropyrrolo[3,2-b][1,5]benzodiazepin-10-one, 1-isopropyl-2,9-dimethyl-1,4,9,10-tetrahydropyrrolo[3,2-b][1,5]benzodiazepin-10-one, 1-(n-butyl)-2,3,9-trimethyl-1,4,9,10-tetrahydropyrrolo[3,2-b][1,5]benzodiazepin-10-one, 1,9-di-(n-butyl)-1,4,9,10-tetrahydropyrrolo[3,2-b][1,5]benzodiazepin-10-one, 2-methyl-9-propyl-1,4,9,10-tetrahydropyrrolo[3,2-b][1,5]benzodiazepin-10-one, 1,2,3-trimethyl-1,4,9,10-tetrahydropyrrolo[3,2-b][1,5]benzodiazepin-10-one, 1,3,9-triethyl-1,4,9,10-tetrahydropyrrolo[3,2-b][1,5]benzodiazepin-10-one, 1,3-di-(n-butyl)-9-ethyl-2-methyl-1,4,9,10-tetrahydropyrrolo[3,2-b][1,5]benzodiazepin-10-one, 9-(tert.-butyl)-1,2-dimethyl-1,4,9,10-tetrahydropyrrolo[3,2-b][1,5]benzodiazepin-10-one, 9-(n-butyl)-1,3-dimethyl-1,4,9,10-tetrahydropyrrolo[3,2-b][1,5]benzodiazepin-10-one, 1-methyl-2-propyl-1,4,9,10-tetrahydropyrrolo[3,2-b][1,5]benzodiazepin-10-one, 9-isopropyl-1,3-dimethyl-1,4,9,10-tetrahydropyrrolo[3,2-b][1,5]benzodiazepin-10-one, 9-methyl-1,4,9,10-tetrahydropyrrolo[3,2-b][1,5]benzodiazepin-10-one, and 1,3-diethyl-9-methyl-1,4,9,10-tetrahydropyrrolo[3,2-b][1,5]benzodiazepin-10-one, and the salts of these compounds with inorganic or organic acids, preferably 1,3-dimethyl-4-pyrrolidinoacetyl-1,4,9,10-tetrahydropyrrolo[3,2-b][1,5]benzodiazepin-10-one and 1,3-dimethyl-4-[(4-methyl-1-piperazinyl)acetyl]-1,4,9,10-tetrahydropyrrolo[3,2-b][1,5]benzodiazepin-10-one and their pharmacologically compatible acid addition salts with inorganic or organic acids.

All of these compounds are prepared according to the hereinafter-described processes from known starting materials or from starting materials which are readily prepared by conventional procedures from available compounds.

The invention furthermore relates to a process for the preparation of tricyclic pyrroles of formula I, wherein $R^2$ is $-CO-C_nH_{2n}-N(R^4)R^5$, and their acid-addition salts with inorganic or organic acids, which is characterized by reacting a pyrrole of formula II

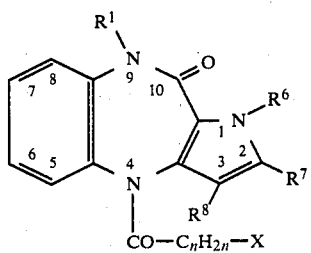

(II)

wherein X represents a halogen atom [compounds (b)] with an amine of formula III

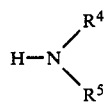

(III)

and, if desired, converting a resulting free base into an acid-addition salt or a resulting acid-addition salt into the corresponding free base.

The reaction of a pyrrole II with an amine III is carried out in an established well-known manner, advantageously in the presence of a proton acceptor. Suitable proton acceptors are, for example, alkali-metal carbonates, such as sodium carbonate or potassium carbonate, or tertiary amines, such as pyridine, triethylamine or ethyldiisopropylamine.

In order to avoid side reactions, it is also advantageous to use an excess of compound III as the proton acceptor. In this case, the reaction is carried out with, for example, a 2-fold to 5-fold excess of the compound III.

The reaction is readily effected in suitable anhydrous solvent, such as a lower alkanol (for example methanol, ethanol or isopropanol), an open-chain or cyclic ether (for example tetrahydrofuran or, in particular, dioxane), an aromatic hydrocarbon (for example benzene or, in particular, toluene) or a chlorinated hydrocarbon (for example methylene chloride), which is advantageously inert.

The reaction temperature is advantageously between 0° and 150° C.; temperatures between 50° and 110° C.—and especially the boiling point of the solvent used—being preferred. Depending on the amine employed, the reaction time is between a few minutes and several hours; if necessary, the reaction is accelerated by adding an alkali-metal iodide to the reaction medium.

If a highly-volatile amine is used, the reaction is preferably carried out at a lower temperature or in a closed apparatus.

Acid-addition salts are obtained by dissolving the free base in a suitable solvent, for example in a chlorinated hydrocarbon, such as methylene chloride or chloroform, or a low-molecular aliphatic alcohol (ethanol or isopropanol), which contains the desired acid or to which the desired acid is subsequently added.

The salts are isolated by filtration, reprecipitation, precipitation with a non-solvent for the addition salts or evaporation of the solvent.

Obtained salts are converted into corresponding free bases by treatment with alkali, for example with aqueous sodium bicarbonate; the free bases are readily converted back into acid-addition salts. In this way, pharmacologically-unacceptable acid-addition salts are converted into pharmacologically-acceptable acid-addition salts. The noted conversions are standard conventional procedures.

Alternatively, compounds of formula I [wherein $R^2$ is $-CO-C_nH_{2n}-N(R^4)R^5$] are obtained by reacting a pyrrole (c) of formula IV

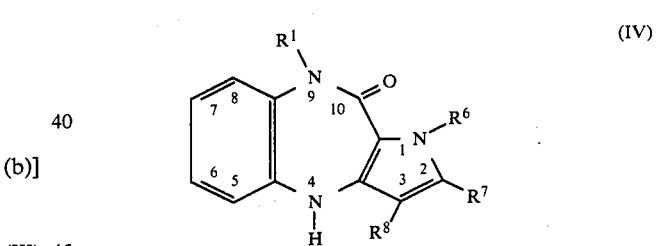

(IV)

with a compound of formula III' (known per se)

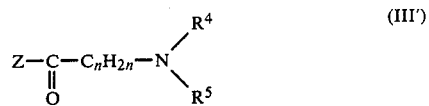

(III')

wherein Z represents a detachable (leaving) group.

Reaction of a compound IV with a compound III' is carried out in a manner which is known per se.

The detachable group Z is a group which, together with the carbonyl group to which it is bonded, forms a reactive carboxylic acid derivative. Examples of reactive carboxylic acid derivatives are acid halides, esters and anhydrides and mixed anhydrides, for example those obtained from the corresponding acid (Z=OH) and a chloroformate or phosphorus oxytrichloride. When Z is a halogen atom, the reaction is advantageously carried out in the presence of an acid-binding agent (proton acceptor). Examples of suitable proton acceptors are alkali-metal carbonates or bicarbonates, such as sodium carbonate or potassium bicarbonate; and tertiary organic amines, such as pyridine, triethylamine or ethyldiisopropylamine.

Detachable or leaving groups are well known to an artisan. The particular detachable or leaving group selected is not the essence of the subject invention, as such groups are generally suitable for the noted purpose.

The reaction of a compound II with a compound III is the preferred process for preparing a compound (a).

Compounds of formula II are obtained by reacting a pyrrole (c) of formula IV

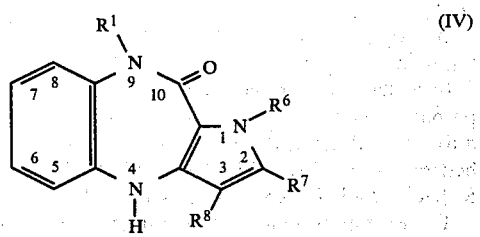

with a compound of formula V

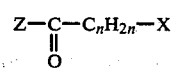

wherein
n is 1 or 2,
X represents a halogen atom and
Z represents a detachable (leaving) group.

Reaction of a pyrrole IV with a compound V is conventionally conducted in a manner which is known per se.

The detachable group Z is, for example, a halogen atom, in particular a chlorine form (—Cl), or the group X—$C_nH_{2n}$—CO—O—. If Z is a halogen atom, the reaction is advantageously carried out in the presence of an acid-binding agent (proton acceptor). Examples of suitable proton acceptors are alkali-metal carbonates or bicarbonates (such as sodium carbonate or potassium bicarbonate) and tertiary organic amines (such as pyridine, triethylamine or ethyldiisopropylamine).

The reaction is preferably carried out in inert, anhydrous solvent. Examples of such solvents are: chlorinated hydrocarbon, such as methylene chloride or chloroform; open-chain or cyclic ether, such as diethyl ether, diethylene glycol dimethyl ether, tetrahydrofuran or, in particular, dioxane; or aromatic hydrocarbon, such as benzene or toluene.

The reaction temperature, which depends on the nature of the detachable group, of the proton acceptor, of the reactants and of the solvent, is generally between 20° and 150° C., in particular between 60° and 110° C., the boiling point of the particular solvent used being preferred. The reaction time varies between 20 minutes and 60 hours.

Compounds of formula IV are obtained in various ways. Thus, compounds IV in which $R^1$ denotes an alkyl radical are obtained in a manner which is known per se by alkylation of the corresponding compound IV in which $R^1$ denotes a hydrogen atom. Suitable bases, for example sodium hydride, sodium amide or potassium t-butanolate, are used for deprotonation of the compound IV in which $R^1$ is a hydrogen atom. The deprotonation is carried out in inert, anhydrous, optionally polar solvents, such as dimethylsulfoxide or dioxane. Subsequent alkylation, for example with a dialkyl sulfate, such as dimethyl sulfate, or with an alkylhalide, such as butyl iodide, leads to the desired products IV in which $R^1$ represents an alkyl radical.

Products IV in which $R^1$ denotes a hydrogen atom and also products IV in which $R^1$ represents an alkyl radical are, moreover, obtained by cyclization of corresponding compounds VI

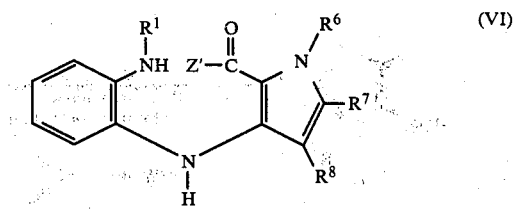

wherein Z' represents a suitable detachable (leaving) group. A suitable detachable group Z' is a group which, together with the carbonyl group to which it is bonded, forms a reactive carboxylic acid derivative. A suitable detachable group Z' is, for example, an alkoxy group, an amino group or a hydroxyl group. The cyclization is carried out in a manner which is known per se—depending on the nature of the detachable group.

When, for example, Z' is an amino group, the cyclization is carried out in the presence or absence of inert, preferably polar, organic solvent, such as lower alkanol, for example, ethanol, if appropriate in the presence of an acid, such as a hydrogen halide acid, or in the presence of a base, for example an alkali-metal alkanolate, at temperatures between 0° and 200° C., preferably at the boiling point of the solvent used. When Z' is an alkoxy group, the cyclization of compounds VI is carried out at temperatures between 0° and 200° C., preferably between 20° and 160° C., in the presence or absence of an inert solvent and, if appropriate, in the presence of a basic or, preferably, acidic catalyst. The reaction times are from 15 minutes to 6 hours. Examples of suitable solvents are alcohols, such as ethanol, isopropanol or glycol; ethers, such as dioxane or diphenyl ether; aromatic hydrocarbons, such as toluene, xylene or o-dichlorobenzene; and dimethylsulfoxide. Suitable catalysts include basic catalysts, such as alkali-metal alkanolates, for example sodium ethylate or potassium tert.-butanolate, or, preferably, sodium hydride; or acidic catalysts, such as organic or inorganic acids, for example acetic acid, chloroacetic acid, p-toluenesulfonic acid, o-chlorobenzoic acid, p-toluic acid, nicotinic acid, trifluoroacetic acid, fumaric acid, hydrochloric acid, benzoic acid or potassium bisulfate, but preferably phosphoric acid, optionally several moles of acidic catalyst being used per mole of starting compound.

When Z' is a hydroxyl group, the cyclization of the compounds VI is carried out, for example, in polar solvent, preferably under acid catalysis, and advantageously in the presence of a condensing agent, such as cyclohexylcarbodiimide, or with continuous removal of the water formed during the reaction, for example by azeotropic entrainment of the water using a water separator. The reaction is preferably carried out at temperatures between 50° and 200° C., in particular at temperatures between 100° and 160° C.

Compounds of formula VI are obtained by reacting an o-halonitrobenzene VII with a pyrrole VIII

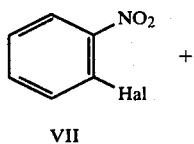

VII

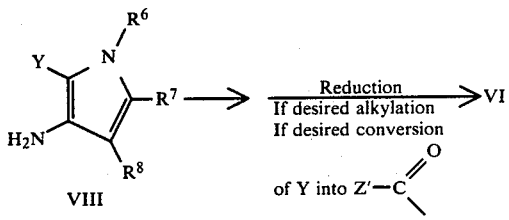

VIII (wherein

Hal represents a halogen atom—in particular a fluorine or chlorine atom,

Y represents a

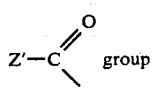 group or a precursor of a

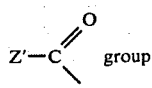 group and $R^6$, $R^7$ and $R^8$ have their previously-ascribed meanings) subsequent reduction of the nitro group to the amino group, if desired subsequent conversion of the radical Y into a suitable radical

and/or if desired subsequent introduction of the alkyl radical $R^1$. (These are all conventional procedures).

A precursor of a

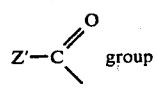 group (=Y) is a substituent which can be converted into the

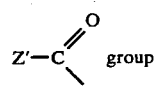 group by a suitable process step familiar to the expert (for example hyrolysis, alcoholysis, acidification and saponification). Preferred precursors Y are the nitrile group (—CN) and the carboxylate group (—COO$^\ominus$), which can be converted into an amide group, ester group or a carboxylic acid radical by hydrolysis, alcoholysis or acidification.

The reaction of a o-halonitrobenzene VII with a pyrrole VIII is carried out in a manner which is known per se, preferably with the addition of a deprotonating agent, for example sodium hydride, potassium carbonate or a tertiary amine, in solvent, such as dimethylformamide, dioxane, tetrahydrofuran or N-methyl-pyrrolidone, and, depending on the nature of the radical Hal in VII and depending on the nature of the deprotonating agent used, at a temperature between 0° and 150° C.

The optional subsequent alkylation is carried out in the manner described for a compound IV.

Pyrroles of formula VIII are known, or they are prepared by a method analogous to published procedures [Mu-Ill Lim, Rovert S. Klein, Jack J. Fox, Tetrahedron Letters 21, 1013 (1980) and Mu-Ill Lim, Robert S. Klein, Jack J. Fox, J. Org. Chem. 44, 3826 (1979)].

The examples which follow illustrate the invention in more detail, without restricting it. The abbreviation m.p. denotes melting point, and D. denotes decomposition point. Reference to "ether" means diethyl ether.

EXAMPLE 1

Ethyl-3-amino-1,4,5-trimethyl-1H-pyrrole-2-carboxylate

A solution of 23.2 g of 1-methyl-2-oxobutyronitrile 27.9 g (0.239 mole) of sarcosine ethyl ester and 0.2 g of p-toluene-sulfonic acid in 200 ml of chloroform is boiled for 2 hours, using a water separator, until no further water is separated out in the condenser. The reaction mixture is then washed with 20 ml of saturated aqueous sodium bicarbonate solution and with 20 ml of water. After drying over sodium sulfate, the resulting mixture is concentrated on a rotary evaporator and the oil which remains is twice taken up in 100 ml of dry ethanol, the solvent in turn being distilled off in vacuo on a rotary evaporator. 300 ml of 1 N sodium ethylate/ethanol solution are poured over the oil which remains, and the mixture is heated under reflux for 2 hours. After the solvent has been stripped off in vacuo, 200 ml of ice-water are added to the solid residue, and the mixture is extracted several times with methylene chloride. When the solvent is stripped off, a solid residue remains; it is recrystallized from diisopropyl ether. Yield: 14.3 g of m.p. 63° to 64° C.

EXAMPLE 2

Potassium-3-amino-1,4,5-trimethyl-1H-pyrrole-2-carboxylate 36.6 g (0.187 mole) of ethyl 3-amino-1,4,5-trimethyl-1H-pyrrole-2-carboxylate and 11.4 g (0.213 mole) of potassium hydroxide are dissolved in 200 ml of methanol, and the obtained solution is boiled under reflux for 4 hours. The resulting solution is concentrated to dryness and used, without further purification, for the next reaction.

EXAMPLE 3

Potassium 1,4,5-trimethyl-3-[(2-nitrophenyl)amino]-1H-pyrrole-2-carboxylate 38 g of 1-chloro-2-nitrobenzene, 38.8 g of potassium 3-amino-1,4,5-trimethyl-1H-pyrrole-2-carboxylate (crude product from Example 2) and 36 g of ground potassium carbonate (particle size: 0.07 mm) are stirred in 120 ml of 1-methyl-2-pyrrolidone under nitrogen at an internal temperature of 140° C. After 12 hours, a further 3.3 g of 1-chloro-2-nitrobenzene are added. For working up, the mixture is filtered hot, and the residue on the filter is rinsed 3 times with 10 ml of hot (100° C.) 1-methyl-2-pyrrolidone each time. The combined filtrates are further processed without purification.

EXAMPLE 4

3-[(2-Aminophenyl)amino]-1,4,5-trimethyl-1H-pyrrole-2-carboxylic acid

The solution of 61 g (0.19 mole) of potassium 1,4,5-trimethyl-3-[(2-nitrophenyl)amino]-1H-pyrrole-2-carboxylate obtained in Example 3 is adjusted to pH 2 with concentrated hydrochloric acid in a circulatory hydrogenation apparatus, and 0.5 g of palladium-on-charcoal (10%) is added. When the internal temperature reaches 40° C., hydrogenation is started. Sufficient hydrogen is metered to keep the internal temperature at about 100° C. When a sudden drop in the absorption of hydrogen is observed, the solution is allowed to cool; it is filtered under nitrogen, and the residue on the filter is washed 6 times with 5 ml of 1-methyl-2-pyrrolidone each time. The combined filtrates are concentrated to half their volume on a rotary evaporator. The resulting solution is subsequently processed in Example 5 without further purification.

EXAMPLE 5

1,2,3-Trimethyl-1,4,9,10-tetrahydropyrrolo[3,2-b][1,5]benzodiazepin-10-one 15 ml of concentrated hydrochloric acid are added to the solution obtained in Example 4, which contains 49.2 g (0.19 mole ) of 3-[(2-aminophenyl)amino]-1,4,5-trimethyl-1H-pyrrole-2-carboxylic acid, and the mixture is heated to an internal temperature of 140° C. for 12 hours. During this heating, the water formed is continuously distilled off. For working up the mixture, as much of the solvent as possible is distilled off on a rotary evaporator under a water-pump vacuum. The residue is taken up in 100 ml of water, and the mixture is adjusted to pH 2, at 80° C., with concentrated hydrochloric acid. The mixture is cooled to 0° C., with stirring. The precipitate formed is filtered off. The filtrate is extracted 3 times with 50 ml of ethyl acetate each time. The combined filtrates are dried with sodium sulfate and concentrated, and the residue is again taken up in 50 ml of water. The resulting mixture is adjusted to pH 2, at 80° C., with concentrated hydrochloric acid. After the mixture has been cooled to 0° C. in an ice-bath, it is filtered. The combined residues on the filter are washed with water and recrystallized from ethyl acetate.

EXAMPLE 6

4-Chloroacetyl-1,2,3-trimethyl-1,4,9,10-tetrahydropyrrolo[3,2-b][1,5]benzodiazepin-10-one A solution of 21 of chloroacetyl chloride in 10 ml of toluene is added dropwise to 31 g of 1,2,3-trimethyl-1,4,9,10-tetrahydropyrrolo[3,2-b][1,5-]benzodiazepin-10-one, 6 g of anhydrous potassium carbonate, 40 ml of dioxane and 20 ml of toluene in the course of 30 minutes at 70° to 80° C., and the thus-prepared mixture is stirred at this temperature for a further 2 hours. The mixture is concentrated to dryness, the residue is boiled 3 times with 25 ml of chloroform each time, and the filtrate is concentrated to dryness. 3.6 g of the title compound are thus obtained.

EXAMPLE 7

1,2,3-Trimethyl-4-[(4-methyl-1-piperazinyl)acetyl]-1,4,9,10-tetrahydropyrrolo[3,2-b][1,5]benzodiazepin-10-one 289 g of 4-chloroacetyl-1,2,3-trimethyl-1,4,9,10-tetrahydropyrrolo[3,2-b][1,5]benzodiazepin-10-one, 200 mg of N-methylpiperazine and 10 ml of dry dioxane are warmed at 70° to 80° C. for 2.5 hours. 10 ml of saturated aqueous sodium bicarbonate solution are added thereto, and the resulting mixture is extracted several times with ethyl acetate. The combined extracts are dried over sodium sulfate and concentrated in vacuo. The resulting oil is taken up in a little dioxane/acetonitrile and is brought to crystallization.

EXAMPLE 8

3-Amino-1,4,5-trimethyl-1H-pyrrole-2-carbonitrile 10.3 ml (0.74 mole) of triethylamine, 7.2 g (0.74 mole) of 3-cyanobutan-2-one and 0.5 g of p-toluenesulfonic acid are successively added to a suspension of 7.8 g (0.74 mole) of N-methylaminoacetonitrile hydrochloride in 70 ml of chloroform, and the mixture is boiled for 5 hours, using a water separator. After it has been boiled, the mixture is washed twice with 10 ml of water each time and dried over sodium sulfate; the solvent is then stripped off in vacuo. In order to remove all of the chloroform, the residue is twice taken up in 100 ml (each time) of dry ethanol, and the mixture concentrated each time in vacuo. The resulting oil is warmed (bath temperature of 50° C.) in 100 ml of 1 N sodium ethylate/ethanol for 2 hours; some of the ethanol is removed. The mixture is then taken up in 100 ml of water and extracted several times with methylene chloride. After being dried over sodium sulfate and concentrated on a rotary evaporator, the extracts yield a solid residue, which is recrystallized from diisopropyl ether.

EXAMPLE 9

Ethyl 3-amino-1,5-dimethyl-1H-pyrrole-2-carboxylate 5.5 g of the title compound are obtained, analogously to Example 1, from 8.3 g (0.1 mole) of 2-oxobutyronitrile and 11.7 g (0.1 mole) of sarcosine ethyl ester.

EXAMPLE 10

Ethyl 1,5-dimethyl-3-(2-nitrophenyl)amino-1H-pyrrole-2-carboxylate 6.0 g (0.2 mole) of commercially available 80% sodium hydride (in paraffin) are added to a solution of 18.2 g (0.1 mole) of ethyl 3-amino-1,5-dimethyl-1H-pyrrole-2-carboxylate in 200 ml of dry dimethylformamide at 0° C. under an inert gas atmosphere ($N_2$). After 1 hour, the evolution of gas has subsided. 28 g (0.2 mole) of 2-fluoronitrobenzene are added dropwise in the course of 30 minutes. After 3 hours, the mixture is allowed to come to room temperature and is poured on to 100 g of ice and extracted several times with ethyl acetate. The combined extracts are washed with water and dried over sodium sulfate. The solvent is stripped off in vacuo. The resulting yellow-orange oil crystallizes completely after a short time. Yield: 22.5 g.

EXAMPLE 11

Ethyl 3-(2-aminophenyl)amino-1,5-dimethyl-1H-pyrrole-2-carboxylate

A catalytic amount of palladium-on-charcoal is added to a solution of 3.0 g (0.01 mole) of ethyl 1,5-dimethyl-3-(2-nitrophenyl)amino-1H-pyrrole-2-carboxylate in 50 ml of ethyl acetate, and the mixture is hydrogenated (in a circulatory hydrogenation apparatus under a slightly elevated pressure at room temperature) until the theoretical amount of hydrogen has been absorbed. After the catalyst has been filtered off, the filtrate is concentrated in vacuo, and the crystalline residue is recrystallized from a little isopropanol. Yield: 2.1 g.

EXAMPLE 12

1,2-Dimethyl-1,4,9,10-tetrahydropyrrolo[3,2-b][1,5]benzodiazepin-10-one 2.73 g (0.01 mole) of ethyl 3-(2-aminophenyl)amino-1,5-dimethyl-1H-pyrrole-2-carboxylate in a solution of 0.25 g (0.011 mole) of sodium in 40 ml of dry ethanol are boiled under reflux for 2 hours. After the mixture has cooled, it is neutralized carefully with acetic acid; the solvent is stripped off in vacuo, and the yellowish residue is recrystallized from dioxane. Yield: 1.9 g.

EXAMPLE 13

4-Chloroacetyl-1,2-dimethyl-1,4,9,10-tetrahydropyrrolo[3,2-b][1,5]benzodiazepin-10-one 1.5 g of the title compound are obtained, analogously to Example 6, from 2.3 g (0.01 mole) of 1,2-dimethyl-1,4,9,10-tetrahydropyrrolo[3,2-b][1,5]benzodiazepin-10-one and 1.6 ml (0.02 mole) of chloroacetyl chloride and after purification on neutral silica gel (methylene chloride).

EXAMPLE 14

1,2-Dimethyl-4-[(4-methylpiperazin-1-yl)acetyl]-1,4,9,10-tetrahydropyrrolo[3,2-b][1,5]benzodiazepin-10-one A solution of 303 mg (0.001 mole) of 4-chloroacetyl-1,2-dimethyl-1,4,9,10-tetrahydropyrrolo[3,2-b][1,5]benzodiazepin-10-one and 200 mg (0.002 mole) of N-methylpiperazine in 10 ml of dry dioxane is boiled under reflux for 2 hours. 20 ml of saturated aqueous sodium bicarbonate solution are added thereto, and then the mixture is extracted several times with ethyl acetate. The combined extracts are dried over sodium sulfate and concentrated in vacuo. The resulting oil is chromatographed on neutral silica gel (methylene chloride/methanol). Yield: 280 mg.

EXAMPLE 15

1,2-Dimethyl-4-piperidinoacetyl-1,4,9,10-tetrahydropyrrolo[3,2-b][1,5]benzodiazepin-10-one 420 mg of the title compound are obtained (analogously to Example 14) from 606 mg (0.002 mole) of 4-chloroacetyl-1,2-dimethyl-1,4,9,10-tetrahydropyrrolo[3,2-b][1,5]benzodiazepin-10-one and 340 mg of piperidine.

EXAMPLE 16

4-Dimethylaminoacetyl-1,2-dimethyl-1,4,9,10-tetrahydropyrrolo[3,2-b][1,5]benzodiazepin-10-one 350 mg of the title compound are obtained (analogously to Example 14) from 606 mg (0.002 mole) of 4-chloroacetyl-1,2-dimethyl-1,4,9,10-tetrahydropyrrolo[3,2-b][1,5]benzodiazepin-10-one and 2 ml of a saturated alcoholic dimethylamine solution.

EXAMPLE 17

1,2,9-Trimethyl-1,4,9,10-tetrahydropyrrolo[3,2-b][1,5]benzodiazepin-10-one 0.33 g (0.011 mole) of 80% sodium hydride (in paraffin) are added to a cold solution (5° C.) of 2.3 g (0.01 mole) of 1,2-dimethyl-1,4,9,10-tetrahydropyrrolo[3,2-b][1,5]benzodiazepin-10-one in 20 ml of dry dimethylsulfoxide and 20 ml of tetrahydrofuran under an inert gas atmosphere ($N_2$). The mixture is stirred for 30 minutes and is allowed to come to room temperature (30 minutes). Thereafter, it is again cooled to 5° C. and 1.4 g (0.01 mole) of methyl iodide, dissolved in 5 ml of dry tetrahydrofuran, are added dropwise. After the mixture has been stirred at 35° C. for 2 hours, 50 ml of ice-water are added, and the mixture is extracted several times with ethyl acetate. The combined extracts are concentrated in vacuo, and the residue is chromatographed on neutral silica gel (methylene chloride/methanol), yield: 1.7 g.

EXAMPLE 18

1,2,9-Trimethyl-4-[(4-methylpiperazin-1-yl)acetyl]-1,4,9,10-tetrahydropyrrolo[3,2-b][1,5]benzodiazepin-10-one 270 mg of the title compound are obtained (analogously to Example 14) from 317 mg (0.001 mole) of 4-chloroacetyl-1,2,9-trimethyl-1,4,9,10-tetrahydropyrrolo[3,2-b][1,5]benzodiazepin-10-one (prepared analogously to Example 6) and 200 mg (0.002 mole) of N-methylpiperazine.

EXAMPLE 19

Ethyl 3-amino-1,4-dimethyl-1H-pyrrole-2-carboxylate 300 mg of 80% sodium hydride are added with stirring at 20° C. to a solution of 9.1 g of N-(2-cyano-1-propenyl)sarcosine ethyl ester (obtained by reacting methacrylonitrile with bromine and subsequent reaction with sarcosine ethyl ester) in 50 ml of anhydrous dimethyl formamide. After warming the reaction mixture to 30° C., an exothermic reaction starts (the temperature rises to 45° C.); this reaction is terminated after 30 minutes. The resulting solution of the title compound (b.p. 70° C., 1.3 Pa) is subsequently processed without further purification.

EXAMPLE 20

Ethyl 1,4-dimethyl-3-(2-nitrophenyl)amino-1H-pyrrole-2-carboxylate

The solution of ethyl 3-amino-1,4-dimethyl-1H-pyrrole-2-carboxylate in dimethyl formamide obtained in Example 19 is cooled to 0° C.; 3.0 g of 80% sodium hydride and 14.1 g of 2-fluoronitrobenzene are added thereto with stirring. After removing the ice-bath, the temperature rises to 40° C. and, simultaneously, an evolution of gas can be observed; this evolution subsides after 3 hours. The mixture is stirred overnight, cooled to 0° C.; 100 g of ice and 100 ml of water are then added. The precipitate formed is filtered off and is washed thoroughly with cold (0° C.) methanol. 13.5 g (87%) of the title compound of m.p. 114° C. (from ethanol) are obtained.

EXAMPLE 21

Methyl 1,4-dimethyl-3-(2-nitrophenyl)amino-1H-pyrrole-2-carboxylate

The title compound of m.p. 110° to 113° C. (from isopropanol) is obtained (analogously to Example 20) from methyl-3-amino-1,4-dimethyl-1H-pyrrole-2-carboxylate and 2-chloronitrobenzene.

EXAMPLE 22

Ethyl 3-(2-aminophenyl)amino-1,4-dimethyl-1H-pyrrole-2-carboxylate

A suspension of Raney nickel in ethanol is added to a warm solution (50° C.) of 80 g of ethyl 1,4-dimethyl-3-(2-nitrophenyl)amino-1H-pyrrole-2-carboxylate and 30 ml of hydrazine hydrate in 2 l of ethanol in such portions that a temperature of 70° C. is not exceeded. After 45 minutes nitrogen evolution is no longer observed when Raney nickel is added. The Raney nickel is filtered off hot and is washed with ethanol. After concentration of the filtrate, 58 g (82%) of the title compound of m.p. 90° C. (from isopropanol) are obtained.

EXAMPLE 23

1,3-Dimethyl-1,4,9,10-tetrahydropyrrolo[3,2-b][1,5]benzodiazepin-10-one 10 g of ethyl 3-(2-aminophenyl)amino-1,4-dimethyl-1H-2-carboxylate and 30 ml of 85% phosphoric acid are mixed thoroughly in a flask and are heated to 90° C. under a water-pump vacuum. After 15 minutes the mixture is allowed to cool. 50 g of ice and 100 ml of water are added, and the yellow precipitate formed is filtered off. 8.1 g (98%) of the title compound of m.p. 184° C. (from isopropanol) are thus obtained.

EXAMPLE 24

4-Chloroacetyl-1,3-dimethyl-1,4,9,10-tetrahydropyrrolo[3,2-b][1,5]benzodiazepin-10-one A solution of 1.47 g of chloroacetyl chloride in 20 ml of dioxane is added dropwise with stirring to 1.9 g of 1,3-dimethyl-1,4,9,10-tetrahydropyrrolo[3,2-b][1,5]benzodiazepin-10-one, 5.5 g of powdered anhydrous potassium carbonate and 50 ml of dioxane in the course of 10 minutes at 50° C. The obtained mixture is stirred for several hours; precipitate is then filtered off, and the filtrate is concentrated to dryness. 1.75 g (69%) of the title compound of m.p. 267° to 269° C. (from acetonitrile) are obtained.

EXAMPLE 25

1,3-Dimethyl-4-[(4-methyl-1-piperazinyl)acetyl]-1,4,9,10-tetrahydropyrrolo[3,2-b][1,5]benzodiazepin-10-one A solution of 1.75 g of 4-chloroacetyl-1,3-dimethyl-1,4,9,10-tetrahydropyrrolo[3,2-b][1,5]benzodiazepin-10-one and 1.15 g of N-methylpiperazine in 50 ml of dry dioxane is warmed at 50° C. for 5 hours with stirring. After the mixture has cooled, the precipitate formed is filtered off. The filtrate is concentrated, 50 ml of saturated sodium bicarbonate solution are added, and the thus-prepared mixture is extracted several times with ethyl acetate. The combined extracts are dried over sodium sulfate and concentrated. 1.5 g of the title compound of m.p. 205° to 207° C. (from ethyl acetate) are obtained. M.p. of the dihydrochloride: 212° C. (D., from water). M.p. of the hemifumarate: 173° C. (from ethanol).

EXAMPLE 26

1,3-Dimethyl-4-piperidinoacetyl-1,4,9,10-tetrahydropyrrolo[3,2-b][1,5]benzodiazepin-10-one The title compound of m.p. 198° C. (from isopropanol) is obtained (analogously to Example 25) from 4-chloroacetyl-1,3-dimethyl-1,4,9,10-tetrahydropyrrolo[3,2-b][1,5]benzodiazepin-10-one and piperidine. M.p. of the hydrochloride: 285° C. (D., from dioxane).

EXAMPLE 27

1,3-Dimethyl-4-pyrrolidinoacetyl-1,4,9,10-tetrahydropyrrolo[3,2-b][1,5]benzodiazepin-10-one The title compound of m.p. 209° to 212° C. (from isopropanol) is obtained (analogously to Example 25) from 4-chloroacetyl-1,3-dimethyl-1,4,9,10-tetrahydropyrrolo[3,2-b][1,5]benzodiazepin-10-one and pyrrolidine. M.p. of the hydrochloride: 218° to 220° C. (from isopropanol).

EXAMPLE 28

1,3-Dimethyl-4-[N-(2-dimethylaminoethyl)amino]acetyl-1,4,9,10-tetrahydropyrrolo[3,2-b][1,5]benzodiazepin-10-one The title compound of m.p. 176° to 180° C. (from acetonitrile) is obtained (analogously to Example 25) from 4-chloroacetyl-1,3-dimethyl-1,4,9,10-tetrahydropyrrolo[3,2-b][1,5]benzodiazepin-10-one and N,N-dimethylethylenediamine.

EXAMPLE 29

1,3-Dimethyl-4-morpholinoacetyl-1,4,9,10-tetrahydropyrrolo[3,2-b][1,5]benzodiazepin-10-one The title compound of m.p. 208° to 210° C. (from ethanol) is obtained (analogously to Example 25) from 4-chloroacetyl-1,3-dimethyl-1,4,9,10-tetrahydropyrrolo[3,2-b][1,5]benzodiazepin-10-one and morpholine.

EXAMPLE 30

1,3-Dimethyl-4-(1-piperazinyl)acetyl-1,4,9,10-tetrahydropyrrolo[3,2-b][1,5]benzodiazepin-10-one The title compound of m.p. 205° to 208° C. (from ethanol) is obtained (analogously to Example 25) from 4-chloroacetyl-1,3-dimethyl-1,4,9,10-tetrahydropyrrolo[3,2-b][1,5]benzodiazepin-10-one and piperazine.

EXAMPLE 31

4-Ethylaminoacetyl-1,3-dimethyl-1,4,9,10-tetrahydropyrrolo[3,2-b][1,5]benzodiazepin-10-one 1.5 g (75%) of the title compound of m.p. 175° to 176° C. (from acetonitrile) are obtained by passing ethylamine into a boiling solution of 4-chloroacetyl-1,3-dimethyl-1,4,9,10-tetrahydropyrrolo[3,2-b][1,5]benzodiazepin-10-one in ethanol.

EXAMPLE 32

1,3-Dimethyl-4-di-(n-propyl)aminoacetyl-1,4,9,10-tetrahydropyrrolo[3,2-b][1,5]benzodiazepin-10-one The title compound of m.p. 176° to 177° C. (from acetonitrile) is obtained (analogously to Example 25) from 4-chloroacetyl-1,3-dimethyl-1,4,9,10-tetrahydropyrrolo[3,2-b][1,5]benzodiazepin-10-one and di-(n-propyl)amine at a reaction temperature of 80° C.

EXAMPLE 33

1,3-Dimethyl-4-dimethylaminoacetyl-1,4,9,10-tetrahydropyrrolo[3,2-b][1,5]benzodiazepin-10-one The title compound of m.p. 219° to 220° C. (from isopropanol) is obtained (analogously to Example 25) by reaction of 4-chloroacetyl-1,3-dimethyl-1,4,9,10-tetrahydropyrrolo[3,2-b][1,5]benzodiazepin-10-one with an excess of dimethylamine at room temperature.

EXAMPLE 34

4-Diethylaminoacetyl-1,3-dimethyl-1,4,9,10-tetrahydropyrrolo[3,2-b][1,5]benzodiazepin-10-one The title compound of m.p. 174° to 175° C. (from isopropanol) is obtained (analogously to Example 25) by reaction of 4-chloroacetyl-1,3-dimethyl-1,4,9,10-tetrahydropyrrolo[3,2-b][1,5]benzodiazepin-10-one with diethylamine at 80° C.

EXAMPLE 35

4-(3-Bromopropionyl)-1,3-dimethyl-1,4,9,10-tetrahydropyrrolo[3,2-b][1,5]benzodiazepin-10-one A solution of 3.42 g of 3-bromopropionyl chloride in 20 ml of dioxane is added dropwise to 4.54 g of 1,3-dimethyl-1,4,9,10-tetrahydropyrrolo[3,2-b][1,5]benzodiazepin-10-one, 5.0 g of powdered anhydrous potassium carbonate and 80 ml of dry dioxane in the course of 10 minutes at from 50° to 60° C., and the mixture is stirred at this temperature for a further 2 hours. The solvent is stripped off in vacuo, and the resulting solid residue is stirred with 300 ml of ice water and filtered off. 5.1 g of the title compound of m.p. 194° to 195° C. (D.) are obtained after recrystallization from isopropanol.

EXAMPLE 36

4-(2-Bromopropionyl)-1,3-dimethyl-1,4,9,10-tetrahydropyrrolo[3,2-b][1,5]benzodiazepin-10-one The title compound of m.p. 245° to 246° C. (D., from isopropanol) is obtained (analogously to Example 35) from 1,3-dimethyl-1,4,9,10-tetrahydropyrrolo[3,2-b][1,5]benzodiazepin-10-one and 2-bromopropionyl chloride.

EXAMPLE 37

1,3-Dimethyl-4-[3-(4-methyl-1-piperazinyl)propionyl]-1,4,9,10-tetrahydropyrrolo[3,2-b][1,5]benzodiazepin-10-one 1.5 g of 4-(3-bromopropionyl)-1,3-dimethyl-1,4,9,10-tetrahydropyrrolo[3,2-b][1,5]benzodiazepin-10-one and 0.85 g of N-methylpiperazine are warmed at 80° C. for 15 hours in 50 ml of dioxane. The thus-obtained mixture is concentrated to dryness in vacuo. 20 ml of saturated aqueous sodium carbonate solution are added thereto with stirring, and the mixture is then extracted three times with ethyl acetate. The combined extracts are dried over sodium sulfate, and the solvent is stripped off in vacuo. The resulting residue is chromatographed on neutral silica gel (methylene chloride/methanol 95/05). 1.2 g of the title compound of m.p. 187° C. (from isopropanol) are obtained).

EXAMPLE 38

1,3-Dimethyl-4-(3-pyrrolidinopropionyl)-1,4,9,10-tetrahydropyrrolo[3,2-b][1,5]benzodiazepin-10-one 1.9 g of 4-(3-bromopropionyl)-1,3-dimethyl-1,4,9,10-tetrahydropyrrolo[3,2-b][1,5]benzodiazepin-10-one and 0.75 g of pyrrolidine are warmed at 80° C. for 4 hours in 50 ml of dioxane. After the solvent has been stripped off in vacuo, the residue is taken up in a little saturated sodium carbonate solution. The mixture is extracted three times with 30 ml of ethyl acetate each time, the combined extracts are dried over sodium sulfate, and the solvent is stripped off in vacuo. The remaining crystalline residue is recrystallized from a little acetonitrile. Yield: 1.5 g of the title compound of m.p. 185° C.

EXAMPLE 39

1,3-Dimethyl-4-(3-dimethylaminopropionyl)-1,4,9,10-tetrahydropyrrolo[3,2-b][1,5]benzodiazepin-10-one The title compound of m.p. 175° C. (from acetonitrile) is obtained analogously to Example 38 by reaction of 4-(3-bromopropionyl)-1,3-dimethyl-1,4,9,10-tetrahydropyrrolo[3,2-b][1,5]benzodiazepin-10-one with dimethylamine.

EXAMPLE 40

1,3-Dimethyl-4-(2-pyrrolidinopropionyl)-1,4,9,10-tetrahydropyrrolo[3,2-b][1,5]benzodiazepin-10-one The title compound of m.p. 213° to 215° C. (from isopropanol) is obtained (analogously to Example 38) by reaction of 4-(2-bromopropionyl)-1,3-dimethyl-1,4,9,10-tetrahydropyrrolo[3,2-b][1,5]benzodiazepin-10-one with pyrrolidine.

EXAMPLE 41

1,3-Dimethyl-4-[2-(4-methyl-1-piperazinyl)propionyl]-1,4,9,10-tetrahydropyrrolo[3,2-b][1,5]benzodiazepin-10-one The title compound is obtained (analogously to Example 38) from 4-(2-bromopropionyl)-1,3-dimethyl-1,4,9,10-tetrahydropyrrolo[3,2-b][1,5]benzodiazepin-10-one and N-methylpiperazine. M.p. 204° to 205° C. (from acetonitrile).

EXAMPLE 42

1,3-Dimethyl-4-[(4-methyl-1-piperazinyl)acetyl]-1,4,9,10-tetrahydropyrrolo[3,2-b][1,5]benzodiazepin-10-one A mixture of 1.00 g of (4-methylpiperazin-1-yl)acetic acid and 0.20 g of 75 percent sodium hydride (in paraffin oil) in 16 ml of dimethylformamide is warmed at from 50° to 80° C. until the evolution of hydrogen has ended (2 to 3 hours). 1.40 g of 1,3-dimethyl-1,4,9,10-tetrahydropyrrolo[3,2-b][1,5]benzodiazepin-10-one are added to the sodium salt formed from the acid, and 0.99 g of 98% pure phosphorous oxychloride are added dropwise at −10° C. in the course of 10 minutes. The batch is stirred at −10° C. for 4 hours, at 0° C. for 4 hours and at room temperature for 20 hours. It is poured onto ice, adjusted to pH 3.5 with sodium hydroxide solution and extracted by shaking with methylene chloride. The aqueous phase is adjusted to pH 9 and extracted by shaking again with methylene chloride. The organic phase is washed with water and concentrated in vacuo. 0.62 g of the title compound of m.p. 205° to 207° C. (fromethyl acetate) are thus obtained.

EXAMPLE 43

1,3-Dimethyl-4-pyrrolidinoacetyl-1,4,9,10-tetrahydropyrrolo[3,2-b][1,5]benzodiazepin-10-one 1.1 g of ethyl chloroformate are added dropwise at 0° C. to a suspension of 1.29 g of pyrrolidin-1-ylacetic acid in 20 ml of tetrahydrofuran. 2.28 g of 1,3-dimethyl-1,4,9,10-tetrahydropyrrolo[3,2-b][1,5]benzodiazepin-10-one are added to the obtained suspension. The mixture is stirred 1 hour at 0° C. and a further 4 hours at room temperature. It is then poured onto 160 ml of 2 N sodium hydroxide solution and extracted with toluene. The organic phase is concentrated to dryness. The residue is chromatographed over a silica gel column by means of a mixture of dioxane/methanol (1:1) to yield 2.1 g of the title compound of m.p. 210° to 212° C. (from isopropanol).

Commercial Usefulness

The tricyclic pyrroles of formula I, those of embodiments (a), (b), and (c), and their acid-addition salts have valuable properties which render them commercially useful.

The tricyclic pyrroles of formula I [wherein $R^2$ represents the group $—CO—C_nH_{2n}—R^3$ and $R^3$ represents the group $—N(R^4)R^5$ and wherein $R^1$, $R^4$, $R^5$, $R^6$, $R^7$, $R^8$ and n have their assigned meanings], pyrroles (a) and their acid-addition salts are pharmacologically-active compounds which are characterized by an excellent protection action on the stomach and intestines of warm-blooded animals. In particular, they inhibit the formation of gastric and intestinal ulcers.

Furthermore, as a result of their low toxicity and the absence of significant side-effects, they have an advantageous therapeutic range. Moreover, the compounds have only a slight anticholinergic action, which can be detected, for example, in the slight inhibition of salivation triggered off by carbachol.

The tricyclic pyrroles of formula I, wherein $R^2$ represents a hydrogen atom ($—H$) or the group $—CO—C_nH_{2n}—R^3$ and $R^3$ is a halogen atom, and pyrroles (b) and (c) are valuable intermediate products for the preparation of the pharmacologically-active compounds. These intermediates provide tricyclic pyrroles (a) and their acid-addition salts with structure which imparts the favorable pharmacological utility to the noted end products.

The excellent activity of the pharmacologically-active tricyclic pyrroles and of their pharmacologically-acceptable acid-addition salts enables them to be used in human medicine or veterinary medicine, where they are used for the treatment and prophylaxis of illnesses based on diseases of the stomach and intestine. For example, acute and chronic ulcus ventriculi and ulcus duodeni, gastritis, hyperacid gastric irritation and stomach complaints caused by medicaments are treated in humans and animals with these compounds or with medicament compositions containing these compounds.

The invention thus furthermore relates to a process for treating animals suffering from one of the previously-mentioned illnesses. This aspect of the invention is characterized by administering an effective amount of a therapeutically-active and pharmacologically-acceptable compound of formula I (or a physiologically-acceptable salt thereof) to a sick mammal afflicted with or prone to the noted illnesses.

The invention also relates to the use of the subject pharmacologically-active compounds in combating the indicated illnesses. The invention likewise comprises the use of the pharmacologically-active compounds in the preparation of medicaments for combating the mentioned illnesses.

The invention furthermore relates to medicaments which contain one or more tricyclic pyrroles (a) and/or their pharmacologically-acceptable acid-addition salts with inorganic or organic acids.

The medicaments are prepared by standard recognized processes. As medicaments, the compounds according to the invention are employed either on their own or, preferably, in combination with suitable known pharamceutical excipients. When the new pharmaceutical formulations contain pharmaceutical excipients in addition to one or more compounds according to the invention, the content of active compound in the resulting compositions is from 0.5 to 95, preferably from 15 to 75, percent by weight of the total.

In accordance with the invention the active compounds are used (in the field of human medicine and in that of veterinary medicine) in any form suitable to establish and/or maintain a sufficient blood or tissue level of active compound. This is achieved, for example, by oral, rectal or parenteral administration in suitable doses. The pharmaceutical formulation of active compound is usually in the form of unit doses appropriate for the desired administration. A unit dose is, for example, a tablet, a dragee, a capsule, a suppository or a measured volume of a powder, of a granular material, of a solution, of an emulsion or of a suspension.

"Unit dose" in the context of the present invention means a physically-determined unit which contains an individual amount of active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain, e.g., from about 0.1 to 500 mg (advantageously from 0.5 to 100 mg and, in particular, from 1 to 30 mg) of active compound.

It is advantageous in human medicine to administer the active compound or compounds (when these are given orally) in a daily dose of from about 0.01 to about 5, preferably from 0.05 to 2.5 and, in particular, from 0.1 to 1.5 mg/kg of body weight, generally in the form of several, preferably 1 to 3, individual administrations in order to achieve the desired results. An individual administration contains the active compound or compounds in an amount of from about 0.01 to about 2.5, preferably from 0.01 to 1.5 and, in particular, from 0.05 to 0.5, mg/kg of body weight. Similar dosages are used for parenteral, for example intravenous, treatment.

The therapeutic administration of the pharmaceutical formulation is effected 1 to 4 times daily at fixed or varying points in time, for example before each meal and/or in the evening. However, it may be necessary to deviate from the mentioned dosages in view of the condition, body weight and age of the individual to be treated, the nature and severity of the illness, the nature of the formulation and of the administration of the medicament, the frequency of administration and the time or interval over which administration takes place. Thus, in some cases less than the suggested amount of active compound is sufficient, whereas the indicated amount of active compound must be exceeded in other cases.

The optimum dosage and method of administration of the active compounds required in each particular case are readily determined by those of ordinary skill in the art on the basis of their expertise.

The pharmaceutical formulations preferably comprise an active compound according to the invention and non-toxic, pharmaceutically-acceptable medicinal excipients (which are used as an admixture or diluent in solid, semi-solid or liquid form, or as a means of encasing, for example in the form of a capsule, a tablet coating, a sachet or some other container for the therapeutically-active ingredient). An excipient optionally serves as a promoter of the resorption of the medicament by the body, as a formulating auxiliary, as a sweetener, as a flavor correctant, as a colorant or as a preservative.

Examples of oral dosages forms are tablets, dragees, hard and soft capsules, for example made of gelatin, dispersible powders, granules, aqueous and oily suspensions, emulsions, solutions or syrups.

Tablets contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are optionally provided with a coating. Delayed dissolution and resorption of the medicament in the gastrointestinal tract and hence, for example, better toleration, a protracted effect or a delayed effect are optionally achieved by tablet coatings. Gelatin capsules generally contain the medicament mixed with a diluent, for example a solid diluent, such as calcium carbonate or kaolin, or an oily diluent, such as neutral oil, olive oil, groundnut oil or paraffin oil.

Aqeusous suspensions optionally contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavoring agents; and sweeteners, for example sucrose, lactose, sodium cyclamate, dextrose or invert sugar syrup.

Oily suspensions contain, for example, groundnut oil, olive oil, sesame oil, coconut oil or paraffin oil, and thickeners, such as beeswax, hard paraffin or cetyl alcohol; and furthermore, sweeteners, flavoring agents and antioxidants.

Emulsions contain, for example, olive oil, groundnut oilor paraffin oil, in addition to emulsifying agents, such as gum acacia, gum tragacanth, phosphatides, sorbitan monooleate or polyoxyethylene sorbitan monooleate, and sweeteners and flavoring agents.

For rectal administration of the medicaments, suppositories, which are prepared with the aid of binders (which melt at rectal temperature), for example cacao butter or polyethylene glycol, are used.

For parenteral administration of the medicaments, sterile injectable aqueous suspensions, isotonic salt solutions or other solutions which contain dispersing agents or wetting agents and/or pharmacologically-acceptable diluents, for example propylene glycol or butylene glycol, are used.

The active compound or compounds are alternatively formulated in a micro-encapsulated form, optionally with the addition of the medtioned excipients or additives.

When the substituted tetrahydropyrrolobenzodiazopinones according to the invention and/or their pharmacologically-acceptable acid-addition salts are employed for treating the stated illnesses, the pharmaceutical formulations optionally also contain one or more pharmacologically-active ingredients from other groups of medicaments, such as antacids, for example aluminum hydroxide and magnesium aluminate; secretion inhibitors, such as $H_2$-blockers, for example cimetidine; gastric and intestinal therapeutics, for example metoclopramide, bromopride and tiapride; tranquilizers, such as benzodiazepines, for example diazepam; spasmolytic agents, for example bietamiverine and camylofin; anticholinergic agents, for example oxyphencyclimine and phencarbamide; glucocorticoids, such as prednisolone, fluocortolne and betamethasone; non-steroidal antiphlogistic agents, such as arylacetic acids and arylpropionic acids and hetero-arylacetic acids and hetero-arylpropionic acids, benzothiazinecarboxamide dioxides, pyrazolidinediones and quinazolinones, for example ibuprofen, naproxen, diclofenac, fenufen, indomethacin, lonazolac, sudoxicam, piroxicam, phenylbutazone, bumadizone calcium and proquazone; and local anaesthetics, for example tetracaine and procaine; and, if appropriate, also enzymes, vitamins, aminoacids and the like.

The active compounds are formulated, for example, in the following manner:

(a) Tablets containing 20 mg of active compound 10 kg of 1,3-dimethyl-4-[(4-methyl-1-piperazinyl)acetyl]-1,4,9,10-tetrahydropyrrolo[3,2-b][1,5]benzodiazepin-10-one, 45 kg of lactose, 31 kg of maize starch and 3 kg of polyvinylpyrrolidone are moistened with about 20 liters of water, and the mixture is granulated through a sieve of 1.25 mm mesh width. The granules are dried in a fluidized bed drier to a moisture content of from 50 to 60%, and 8 kg of sodium carboxymethylcellulose, 2 kg of talc and 1 kg of magnesium stearate are then added. The finished granules are pressed to tablets weighing 200 mg and having a diameter of 8 mm.

(b) Capsules with an active compound content of 15 mg 150 mg of 1,3-dimethyl-4-[(pyrrolidino)acetyl]-1,4,9,10-tetrahydropyrrolo[3,2-b][1,5]benzodiazepin-10-one, 845 g of microcrystalline cellulose and 1 g of amorphous silicic acid are finely powdered and mixed thoroughly. Size 4 hard gelatin capsules are filled with the mixture.

Pharmacology

The excellent protection action on the stomach shown by the pharmacologically-active tricyclic pyrroles is demonstrated by a test using so-called Shay rats as a model. The compounds according to the invention prove to have a protective action on the stomach and a therapeutic range which are clearly superior to those of the known commercial product, carbenoxolone.

The substances investigated in this test are characterized in the table which follows by means of serial numbers which are allocated as follows:

| Serial No. | Name of Compound |
|---|---|
| 1 | Carbenoxolone |
| 2 | 1,3-Dimethyl-4-[(4-methyl-1-piperazinyl)acetyl]-1,4,9,10-tetrahydropyrrolo[3,2-b][1,5]benzodiazepin-10-one |
| 3 | 1,3-Dimethyl-4-piperidinoacetyl-1,4,9,10-tetrahydropyrrolo[3,2-b][1,5]benzodiazepin-10-one |
| 4 | 1,3-Dimethyl-4-pyrrolidinoacetyl-1,4,9,10-tetrahydropyrrolo[3,2-b][1,5]benzodiazepin-10-one |
| 5 | 4-Diethylaminoacetyl-1,3-dimethyl-1,4,9,10-tetrahydropyrrolo[3,2-b][1,5]benzodiazepin-10-one |
| 6 | 1,3-Dimethyl-4-dimethylaminoacetyl-1,4,9,10-tetrahydropyrrolo[3,2-b][1,5]benzodiazepin-10-one |
| 7 | 1,3-Dimethyl-4-di-n-propylaminoacetyl-1,4,9,10-tetrahydropyrrolo[3,2-b][1,5]benzodiazepin-10-one |
| 8 | 4-Ethylaminoacetyl-1,3-dimethyl-1,4,9,10-tetrahydropyrrolo[3,2-b][1,5]benzodiazepin-10-one |
| 9 | 1,3-Dimethyl-4-(3-pyrrolidino-propionyl)-1,4,9,10-tetrahydropyrrolo[3,2-b][1,5]benzodiazepin-10-one |
| 10 | 1,3-Dimethyl-4-(3-dimethylamino-propionyl)-1,4,9,10-tetrahydropyrrolo[3,2-b][1,5]benzodiazepin-10-one |

The effect of the compounds according to the invention on the formation, in rats, of gastric ulcers provoked by a pylorus ligature and 10 mg/kg of acetylsalicylic acid and on the inhibition of gastric secretion in rats is shown in the following table:

| Antiulcerogenic action and toxicity of tricyclic pyrroles | | | |
|---|---|---|---|
| Serial No. | Toxicity $LD_{50}$[mg/kg], intravenous administration to mice | Protective action on the stomach $ED_{50}$[mg/kg], peroral administration to rats | TQ $LD_{50}/ED_{50}$ | Gastric Secretion(+) % inhibition in rats |
| 1 | 290 | 70 | 4.1 | 7 |
| 2 | 100 | 1.4 | 71.4 | 25 |
| 3 | 95 | 4.5 | 21.1 | 3 |
| 4 | 100 | 2.2 | 45.5 | 0 |
| 5 | 105 | 6.0 | 17.5 | 20 |
| 6 |  | 6.5 |  | 10 |
| 7 | 110 | 6.5 | 16.9 | 10 |
| 8 | 140 | 5.5 | 25.5 | 20 |
| 9 | 70 | 6.0 | 11.7 | 25 |
| 10 | 120 | 4.5 | 26.7 | 21 |

$ED_{50}$ = dose which reduces the ulcer index by 50% in the treated group compared with the control group
$LD_{50}$ = dose at which 50% of the animals die
TQ = therapeutic quotient $LD_{50}/ED_{50}$
(+) % inhibition of the gastric secretion (in %) 4 hours after administration of the antiulcerogenic $ED_{50}$ It should be particularly emphasized that an $ED_{50}$ can indeed still be determined in the case of compound 1, but the dose/action curve is then very severely flattened so that no substantial increase in the antiulcerogenic action can be achieved even at 300 mg/kg. In contrast, the action of the compounds according to the invention is strictly dependent on the dose; inhibition effects of up to 99% (30 mg/kg) can be achieved.

The antiulcerogenic action was tested in accordance with the method using the so-called Shay rat: Rats (female, 180 to 200 g, 4 animals per cage on a high grid) which had been fasted for 24 hours were subjected to ulcer provocation by pylorus ligature (under diethyl ether anaesthesia) and oral administration of 100 mg/10 ml/kg of acetylsalicyclic acid. The substances to be tested are administered orally (10 ml/kg) 1 hour before the pylorus ligature. The wound is closed by means of Michel clamps. 4 hours thereafter, the animals are killed under ether anaesthesia by atlas dislocation, and the stomach is removed. The stomach is opened longitudinally and fixed to a cork tile after the amount of gastric juice secreted (volume) has been determined, the number and size (=diameter) of ulcers present are determined with a stereomicroscope with 10-fold magnification. The product of the degree of severity (according to the following rating scale) and the number of ulcers serves as the individual ulcer index.

Scale of points:

| no ulcers | 0 |
|---|---|
| ulcer diameter | 0.1–1.4 mm 1 |
|  | 1.5–2.4 mm 2 |
|  | 2.5–3.4 mm 3 |
|  | 3.5–4.4 mm 4 |
|  | 4.5–5.4 mm 5 |
|  | >5.5 mm 6 |

The reduction in the average ulcer index of each treated group compared with that of the control group (=100%) serves as a measure of the antiulcerogenic effect. The $ED_{50}$ designates the dose which reduces the average ulcer index by 50%.

Determination of toxicity

The toxicity investigations are carried out on female NMRI mice (body weight: 23 to 30 g). The animals (5 animals per dose) receive feed and water ad libitum. Various doses of the substances are administered intravenously (injection time: 1 minute). The observation period is 7 days. The $LD_{50}$ (the dose at which 50% of the animals die) is determined by means of linear regression.

The invention and its advantages are readily appreciated from the preceding description. Various changes may be made in structures of intermediates and final products, in formulations of medicament compositions and in methods of use without departing from the spirit and scope of the invention or sacrificing its material advantages. The described intermediates, final products, acid-addition salts, medicament compositions and methods of use are merely illustrative of preferred embodiments of the invention.

What is claimed is:

1. A tricyclic pyrrole of the formula

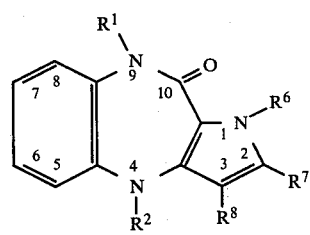

(I)

wherein
$R^1$ is —H or lower alkyl;
$R^2$ is —H or —CO—$C_nH_{2n}$—$R^3$;
$R^3$ is halo or —N($R^4$)$R^5$;

R$^4$ is —H, lower alkyl, alkenyl with from 3 to 5 carbon atoms or, together with R$^5$ and the nitrogen atom to which both are bonded, pyrrolidino, piperidino, morpholino, perhydroazepino, 1-piperazinyl, 4-methyl-1-piperazinyl, 4-ethyl-1-piperazinyl, 4-benzyl-1-piperazinyl, 1-homopiperazinyl or 4-methyl-1-homopiperazinyl;

R$^5$ is alkenyl with from 3 to 5 carbon atoms, lower alkyl, di(lower)alkylamino(lower)alkyl or, together with R$^4$ and the nitrogen atom to which both are bonded, pyrrolidino, piperidino, morpholino, perhydroazepino, 1-piperazinyl, 4-methyl-1-piperazinyl, 4-ethyl-1-piperazinyl, 4-benzyl-1-piperazinyl, 1-homopiperazinyl or 4-methyl-1-homopiperazinyl;

each of R$^6$, R$^7$ and R$^8$ is, independently, —H or lower alkyl; and n is a positive whole number of at most 2;

or an acid-addition salt thereof.

2. A tricyclic pyrrole according to claim 1, wherein each lower alkyl is, independently, an alkyl with from 1 to 4 carbon atoms, or an acid-addition salt thereof with an organic or an inorganic acid.

3. A compound according to claim 2 wherein R$^2$ is —CO—C$_n$H$_{2n}$—R$^3$, and R$^3$ is —N(R$^4$)R$^5$.

4. A compound according to claim 3 wherein
each of R$^1$, R$^6$, R$^7$ and R$^8$ is, independently, —H, —CH$_3$ or —C$_2$H$_5$;
R$^4$ is —H, lower alkyl, alkenyl with 3 carbon atoms or, together with R$^5$ and the nitrogen atom to which both are bonded, pyrrolidino, piperidino, morpholino, piperazino, 4-methyl-1-piperazinyl or 4-ethyl-1-piperazinyl;
R$^5$ is lower alkyl, optionally terminally-substituted by a dimethylamino or diethylamino group, alkenyl with 3 carbon atoms or, together with R$^4$ and the nitrogen atom to which both are bonded, pyrrolidino, piperidino, morpholino, piperazino, 4-methyl-1-piperazinyl or 4-ethyl-1-piperazinyl.

5. A tricyclic pyrrole according to claim 3 wherein
R$^1$ is —H;
R$^4$ is —H, lower alkyl or, together with R$^5$ and the nitrogen atom to which both are bonded, pyrrolidino, piperidino, morpholino, 1-piperazinyl or 4-methyl-1-piperazinyl;
R$^5$ is lower alkyl, optionally terminally-substituted by a dimethylamino group or, together with R$^4$ and the nitrogen atom to which both are bonded, pyrrolidino, piperidino, morpholino, 1-piperazinyl or 4-methyl-1-piperazinyl;
R$^6$ is —CH$_3$;
R$^7$ is —H; and
R$^8$ is —CH$_3$;
or a pharmacologically-compatible acid-addition salt thereof.

6. A tricyclic pyrrole according to claim 3 wherein
R$^1$ is —H;
R$^4$ is —H, —CH$_3$, —C$_2$H$_5$ or —C$_3$H$_7$ or, together with R$^5$ and the nitrogen atom to which both are bonded, pyrrolidino, piperidino or 4-methyl-1-piperazinyl;
R$^5$ is —CH$_3$,—C$_2$H$_5$ or —C$_3$H$_7$ or, together with R$^4$ and the nitrogen atom to which both are bonded, pyrrolidino, piperidino or 4-methyl-1-piperazinyl;
R$^6$ is —CH$_3$;
R$^7$ is —H;
R$^8$ is —CH$_3$; and
n is 1;
or a pharmacologically-compatible acid-addition salt thereof.

7. A compound according to claim 6 which is 1,3-dimethyl-4-pyrrolidino-acetyl-1,4,9,10-tetrahydropyrrolo[3,2-b][1,5]-benzodiazepin-10-one or a pharmacologically-compatible acid-addition salt thereof.

8. A compound according to claim 6 which is 1,3-dimethyl-4-[(4-methyl-1-piperazinyl)acetyl]-1,4,9,10-tetrahydropyrrolo[3,2-b][1,5]benzodiazepin-10-one or a pharmacologically-compatible acid-addition salt thereof.

9. A compound according to claim 2 wherein R$^2$ is —CO—C$_n$H$_{2n}$—R$^3$, and R$^3$ is halo.

10. A compound according to claim 9 wherein each of R$^1$, R$^6$, R$^7$ and R$^8$ is, independently, —H, —CH$_3$ or —C$_2$H$_5$, and R$^3$ is —Cl or —Br.

11. A compound according to claim 9 wherein
R$^1$ is —H;
R$^3$ is —Cl or —Br;
R$^6$ is —CH$_3$;
R$^7$ is —H; and
R$^8$ is —CH$_3$.

12. A compound according to claim 2 wherein R$^2$ is —H.

13. A compound according to claim 12 wherein each of R$^1$, R$^6$, R$^7$ and R$^8$ is, independently, —H, —CH$_3$ or —C$_2$H$_5$.

14. A compound according to claim 12 wherein
R$^1$ is —H;
R$^6$ is —CH$_3$;
R$^7$ is —H; and
R$^8$ is —CH$_3$.

15. A medicament composition comprising excipient or carrier and from 0.5 to 95 percent by weight of a pharmacologically-active and physiologically-acceptable compound according to claim 1 in free-base or acid-addition-salt form.

16. A medicament composition useful for treatment or prophylaxis of illness based on a stomach or intestine disorder, the composition comprising excipient or carrier and an effective amount, per unit dose, of a pharmacologically-active and physiologically-acceptable compound according to claim 3 in free-base or acid-addition-salt form.

17. A method of prophylaxis or treatment of illness based on a stomach or intestine disorder which comprises administering an effective amount of a pharmacologically-active and physiologically-acceptable compound according to claim 3, 4 or 5 to a subject prone to or afflicted with such illness.

* * * * *